US009366600B2

(12) United States Patent
Ruhge

(10) Patent No.: US 9,366,600 B2
(45) Date of Patent: Jun. 14, 2016

(54) LINEAR ARRAY TO IMAGE ROTATING TURBINE COMPONENTS

(71) Applicant: Siemens Energy, Inc., Orlando, FL (US)

(72) Inventor: Forrest R. Ruhge, Orlando, FL (US)

(73) Assignee: SIEMENS ENERGY, INC., Orlando, FL (US)

( * ) Notice: Subject to any disclaimer, the term of this patent is extended or adjusted under 35 U.S.C. 154(b) by 212 days.

(21) Appl. No.: 14/330,224

(22) Filed: Jul. 14, 2014

(65) Prior Publication Data

US 2016/0011078 A1    Jan. 14, 2016

(51) Int. Cl.
*G01M 15/14* (2006.01)
*G01N 21/954* (2006.01)
*G01N 21/17* (2006.01)

(52) U.S. Cl.
CPC ............ *G01M 15/14* (2013.01); *G01N 21/954* (2013.01); *G01N 2021/1774* (2013.01); *G01N 2021/9542* (2013.01)

(58) Field of Classification Search
CPC .................... G01N 21/954; G01N 2021/1774; G01N 2021/9542; G01M 15/14
USPC ................ 73/112.01, 112.02, 112.03, 112.05
See application file for complete search history.

(56) References Cited

U.S. PATENT DOCUMENTS

| 5,884,775 | A | 3/1999 | Campbell | |
|---|---|---|---|---|
| 8,570,505 | B2 | 10/2013 | Baleine et al. | |
| 2003/0042443 | A1 | 3/2003 | Pechan et al. | |
| 2004/0051525 | A1* | 3/2004 | Hatcher | G01N 27/902 324/262 |
| 2005/0199832 | A1 | 9/2005 | Twerdochlib | |
| 2010/0076703 | A1* | 3/2010 | Twerdochlib | G01H 1/006 702/56 |
| 2012/0026306 | A1* | 2/2012 | Mitra | G01N 29/0654 348/61 |
| 2012/0171015 | A1* | 7/2012 | DeLancey | F01D 17/02 415/118 |
| 2013/0083187 | A1 | 4/2013 | Xie et al. | |
| 2013/0093876 | A1* | 4/2013 | Ishizuka | A61B 1/00 348/82 |
| 2013/0194413 | A1* | 8/2013 | Hatcher | G02B 23/2476 348/82 |
| 2013/0335530 | A1 | 12/2013 | Hatcher, Jr. et al. | |
| 2014/0376590 | A1* | 12/2014 | Hwang | G01M 15/14 374/130 |
| 2015/0022655 | A1* | 1/2015 | Ruhge | G02B 23/2423 348/82 |
| 2015/0049396 | A1* | 2/2015 | Lemieux | G02B 23/2492 359/819 |
| 2015/0092039 | A1* | 4/2015 | Ruhge | G01B 21/16 348/82 |
| 2015/0125267 | A1* | 5/2015 | Hatcher, Jr. | F01D 21/003 415/118 |
| 2015/0199805 | A1* | 7/2015 | Hatcher, Jr. | G06T 7/004 348/135 |
| 2015/0341600 | A1* | 11/2015 | Hatcher, Jr. | H04N 7/183 348/82 |

* cited by examiner

Primary Examiner — Eric S McCall

(57) ABSTRACT

A method of inspecting a component located on a rotor rotating about an axis internal to a turbine. An elongated probe is provided defining a probe length and having a one-dimensional pixel array formed by a plurality of pixels extending single file along the probe length. The probe is positioned through an access port in a casing of the turbine. The rotor is rotated to move the component past the pixel array, and energy emitted from an image area defined by a line extending along the component is received at the pixel array. An intensity-based signal from each pixel in the pixel array is conveyed to a processor to convert the intensity-based signals to an intensity-based line image, and a succession of the intensity-based line images are converted into a cohesive two-dimensional digital image of the component.

19 Claims, 3 Drawing Sheets

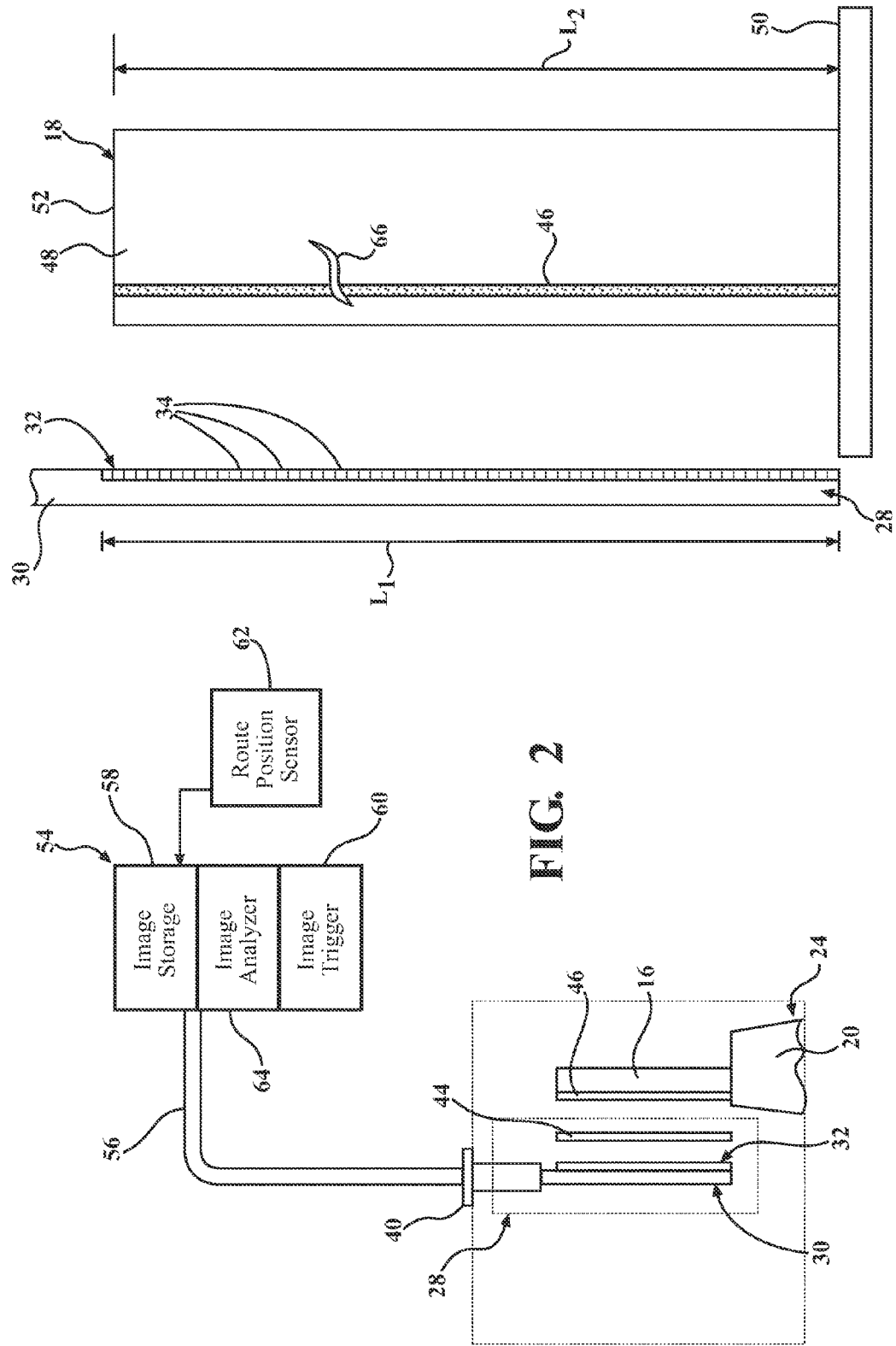

LINEAR ARRAY TO IMAGE ROTATING TURBINE COMPONENTS

FIELD OF THE INVENTION

The present invention relates to the field of inspection of power generation equipment and, more particularly to inspection of turbine blades in a gas turbine engine.

BACKGROUND OF THE INVENTION

In various multistage turbomachines used for energy conversion, such as turbines, a fluid is used to produce rotational motion. In a gas turbine engine, for example, air is compressed through successive stages in a compressor and mixed with fuel in a combustor. The combination of air and fuel is then ignited for generating combustion or hot working gases that are directed to turbine stages to produce the rotational motion. The compressor stages and turbine stages typically have stationary or non-rotary components, e.g., vane structures, that cooperate with rotatable components, e.g., rotor blades, for compressing air and expanding the hot working gases.

The inaccessibility and small size of the open space within the combustion turbine, and between and among the turbine blades, makes inspection of the blades difficult without partial disassembly of the turbine. In-situ inspections can be performed using a borescope or a camera system. Inspection systems using a camera provide images that can be difficult to analyze in that images provided by cameras, such as cameras that utilize CCD imaging matrices, are strongly dependent on the level of contrast between adjacent features being imaged to visualize details of a viewed object. Hence, in the low light environment typically available for in-situ inspection of turbine blades, where it is difficult to provide adequate illumination, conventional camera imaging of the turbine blades may be limited in relation to providing identification of details of interest, such as defects, forming on the turbine blades.

SUMMARY OF THE INVENTION

In accordance with an aspect of the invention, a method of inspecting a component is provided, the component being located on a rotor rotating about an axis internal to a turbine. The method comprises providing an elongated probe defining a probe length and having a one-dimensional pixel array formed by a plurality of pixels extending single file along the probe length; positioning the probe through an access port in a casing of the turbine; rotating the rotor to move the component past the pixel array; receiving at the pixel array energy emitted from an image area defined by a line extending along the component and lying in a plane extending parallel to radial and axial directions in the turbine; conveying an intensity-based signal from each pixel in the pixel array to a processor to convert the intensity-based signals to an intensity-based line image; and converting a succession of the intensity-based line images into a cohesive two-dimensional digital image of the component.

The component may be a turbine blade and the probe may be positioned with the probe length extending radially from the casing toward the rotor. The turbine blade can include a blade length extending from a radially inner platform to a radially outer blade tip, and the pixel array may extend the length of the blade from the platform to the blade tip. The pixel array may have a length of about 12 inches.

Rotation of the rotor can be performed during a turning gear operation of the turbine.

A lens can be positioned between the component and the pixel array, and the lens can focus light energy received from the image area into a line on the pixel array.

The intensity-based signal can be conveyed from the pixel array and conversion to the intensity-based line images can be synchronized to a rotation speed of the rotor.

Elongated red, green and blue filters may extend along the probe length, and a one-dimension pixel array may be associated with each filter and receive energy passing through an associated filter from the component, and the method can include converting a succession of intensity-based line images received from the arrays into a cohesive color image of the component.

In accordance with another aspect of the invention, a system is provided for inspecting a component located on a rotor rotating about an axis internal to a turbine. The system comprises an elongated probe having a one-dimensional pixel array formed by a plurality of pixels extending single file along a length dimension of the probe, wherein the probe is positioned between a casing and a rotor of the turbine and extends in a plane that is parallel to radial and axial directions in the turbine. The pixel array is configured to receive energy emitted from an image area defined by a line extending along the component and lying in the plane of the probe. An array conduit is configured to convey an intensity-based signal from each pixel in the pixel array to a distal end of the array conduit. A processor is connected to the distal end of the array conduit outside of the turbine and configured to convert a succession of the intensity-based signals into a succession of corresponding intensity-based line images for formation of a cohesive two-dimension digital image of the component.

The component may be a turbine blade and the probe may be positioned with the length dimension extending radially from the casing toward the rotor. The turbine blade can include a blade length extending from a radially inner platform to a radially outer blade tip, and the pixel array may extend the length of the blade from the platform to the blade tip. The pixel array can have a length of about 12 inches.

The turbine can include a turning gear operating to rotate the component relative to the probe.

A lens can be positioned between the component and the pixel array, and the lens can be configured to focus light energy received from the image area into a line on the pixel array.

The processor can be configured to synchronize to a rotation speed of the rotor conversion of the intensity-based signals from the pixel array into intensity-based line images.

Elongated red, green and blue filters can extend along the probe length, and a one-dimension pixel array can be associated with each filter and receive energy passing through an associated filter from the component, wherein the processor can be configured to convert a succession of intensity-based line images received from the arrays into a cohesive color image of the component.

The system can further comprise a shaft position signal generator configured to generate a position signal indicating a predetermined rotational position of the rotor, a trigger signal generator associated with the processor configured to transmit trigger signals to the pixels in the pixel array to generate the intensity-based signals of the pixel array, wherein the trigger signal generator transmits a plurality of trigger signals to cause the processor to capture a plurality of intensity-based signals from the pixel array, the trigger signal generator further configured to transmit each of the plurality of trigger signals at a respective time based on the position signal so that each respective trigger signal corresponds to a respective rotational position of the shaft, and the processor including an image analyzer configured to create a two-dimensional image of the rotating component by arranging the plurality of intensity-based line images obtained from the intensity-based signals in order according to the respective corresponding rotational position for each of the plurality of intensity-based line images.

In accordance with a further aspect of the invention, a method of inspecting a turbine blade is provided. The turbine blade is located on a rotor rotating about an axis internal to a turbine, the turbine blade including a radially elongated airfoil supported to a blade platform and defining a blade tip opposite the platform. The method comprises providing an elongated probe defining a probe length and having a one-dimensional pixel array formed by a plurality of pixels extending single file along the probe length, wherein a length of the pixel array is generally the same as a length of the airfoil between the blade platform and the blade tip; positioning the probe through an access port in a casing of the turbine; rotating the rotor to move the turbine blade past the pixel array; receiving at the pixel array energy emitted from an image area defined by a radially extending line extending along the airfoil; conveying an intensity-based signal from each pixel in the pixel array to a processor to convert the intensity-based signals to an intensity-based line image; and converting a succession of the intensity-based line images into a cohesive two-dimensional digital image of the airfoil.

Conveying the intensity-based signal from the pixel array and conversion to the intensity-based line images may be synchronized to a rotation speed of the rotor.

BRIEF DESCRIPTION OF THE DRAWINGS

While the specification concludes with claims particularly pointing out and distinctly claiming the present invention, it is believed that the present invention will be better understood from the following description in conjunction with the accompanying Drawing Figures, in which like reference numerals identify like elements, and wherein:

FIG. 2 is a schematic view including a functional block diagram of an imaging system in accordance with aspects of the present invention;

FIG. 3 is a circumferential view of a probe positioned in relation to a turbine blade during an inspection operation;

DETAILED DESCRIPTION OF THE INVENTION

In the following detailed description of the preferred embodiment, reference is made to the accompanying drawings that form a part hereof, and in which is shown by way of illustration, and not by way of limitation, a specific preferred embodiment in which the invention may be practiced. It is to be understood that other embodiments may be utilized and that changes may be made without departing from the spirit and scope of the present invention.

Figure 1:
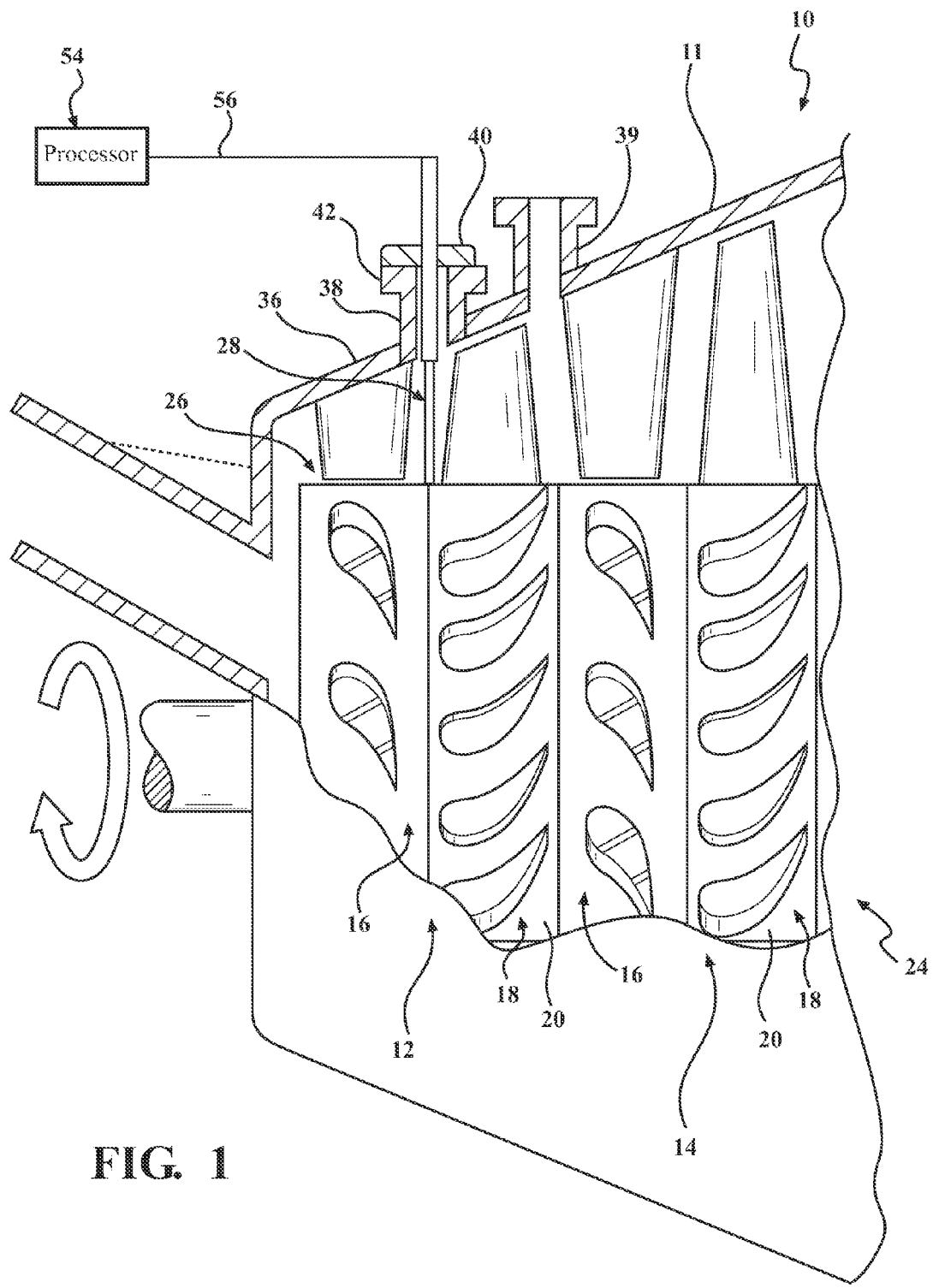
FIG. 1 is a partial cross-sectional schematic view of a gas turbine engine illustrating performance of an inspection operation with a probe in accordance with aspects of the present invention.

Referring initially to FIG. 1, a portion of a turbine engine 10 is illustrated diagrammatically and comprises a turbine 11 including adjoining stages 12, 14, each stage 12, 14 comprising a row of stationary vane assemblies 16 and a row of rotating blades 18, where the vane assemblies 16 and blades 18 are positioned circumferentially in rows within the engine 10 with alternating arrays of vane assemblies 16 and blades 18 located in the axial direction of the turbine engine 10. The blades 18 are supported on rotor disks 20 which may be secured together to define a rotor 24 supported for rotation within the engine 10. The vane assemblies 16 and blades 18 extend into an annular gas passage 26, and hot gases, e.g., from a combustion stage, are directed through the gas passage 26 past the vane assemblies 16 and blades 18.

As mentioned above, visually inspecting areas inside the turbine 11 has proven difficult due to limited access space to locate optical components, as well as due to difficulty in providing adequate light to illuminate areas view by the optical components. In accordance with an aspect of the invention, a system is provided for inspecting rotating components of the turbine 11 including a probe and image processing process to provide improved sensitivity in sensing variations in reflected light from the component, utilizing increased contrast sensitivity to facilitate feature identification on the component.

Referring to FIG. 2, a system in accordance with the invention is illustrated diagrammatically, depicting elements for inspecting a component located on the rotor 24 internal to the turbine 11. The system includes an elongated probe 28 comprising an elongated rod 30 supporting a one-dimensional pixel array 32 (see also FIG. 3) formed by a plurality of pixels 34 extending single file along a length dimension $L_1$ of the probe 28. In the particular embodiment illustrated herein, the elongated probe 28 extends radially, i.e., in the direction of elongation of the blades 18. However, it may be understood that aspects of the invention may be implemented to provide component imaging in additional locations where sensitivity to low contrast light conditions may be required to identify features of interest on components internal to the engine 10.

As seen in FIG. 1, the probe 28 is positioned between the rotor 24 and a casing 36 of the turbine 11 and extends in a plane that is parallel to radial and axial directions in the turbine 11. The probe 28 positions the pixel array 32 within a relatively narrow space, axially between the row of blades 18 and row of vanes 16, and located in facing relationship to the blades 18. In a preferred embodiment of the invention, the probe 28 can be inserted from outside of the engine 10 through an existing inspection port 38 (FIG. 1). In addition, the probe 28 can include a base 40 for cooperating with a flange 42 of the port 38, and can be temporarily fastened, such as by bolts, to the flange 42 to retain the probe 28 in a stationary position relative to the casing 36 throughout an inspection procedure. It may be noted that the turbine 11 can include additional ports, depicted by port 39, that can provide an alternative location to receive the probe 28 or a similar probe.

The probe 28 can further include a focusing element, depicted diagrammatically at 44, located between the row of blades 18 and the pixel array 32. The focusing element 44 can be a lens which, with the pixel array 32, forms an imaging head on the probe 28. The lens (focusing element 44) can be selected so that an image area 46 is defined at component locations, as formed along the blades 18. The image area 46 is defined as a line extending along the blades 18, i.e., on a given blade 18 positioned adjacent to the probe 28, and lying in the plane of the probe 28. That is, the line defining the image area 46 is preferably an imaginary line defined on the blade 18 at a location where a plane containing the probe 28, and in particular containing the pixel array 32, intersects the blade 18.

Referring to FIG. 3, the length $L_1$ of the pixel array 32 is preferably configured to be the same as a length $L_2$ of a radially elongated airfoil 48 of the blade 18, extending from an blade platform 50 at an inner end of the airfoil 48 to a blade tip 52 at a radially outer end of the airfoil 48. Each pixel 34 of the pixel array 32 has a radial location to receive energy, such as reflected light energy, from a corresponding radial location of the image area 46 on the airfoil 48. The pixel array 32 can include several thousand pixels 34 arranged in single file, side-by-side in the radial direction, to image light intensity from the corresponding radial locations along the airfoil 48, as defined along the line of the image area 46. It may be noted that the airfoil 48 is typically formed as a curved surface that has a circumferential component, such that the image area 46 can be located at different locations along the airfoil surface from a leading edge toward trailing edge of the airfoil 48, the particular location of the image area 46 depending upon a rotational position of the blade 18 relative to the probe 28.

The pixels 34 are preferably CMOS active pixel sensors (APS) that can receive light energy emitted, e.g., reflected, from the corresponding radial locations of the image area and provide an intensity-based output signal, where each pixel 34 provides an individual intensity-based output signal depending on how much light energy it receives. That is each pixel 34 can generate an electrical signal output, i.e., a voltage output, that corresponds to an instantaneous intensity of light received at the pixel 34. During an inspection process, the output signals from the pixels 34 are obtained simultaneously and can be conveyed, via an array conduit 56, from the pixel array 32 to a processor 54 at a distal end of the array conduit 56 outside of the turbine 11, as illustrated in FIG. 2. The processor 54 can include image storage 58 where the output signals from the pixels 34 can be stored as a data file in the form of a digitized intensity-based line image comprising a single scan line image of the intensity of light energy received from the linear image area 46. For example, for each pixel in the intensity-based line image, an intensity value of the pixel may be stored. It may be noted that the pixels 34 could alternatively be CCD pixels, however, CMOS pixels provide a preferred sensitivity for the present invention.

The inspection process further includes rotating the rotor 24, such as can be performed during a turning gear operation in which the rotor 24 is rotated at a speed of about 2-3 rpm. Rotation of the rotor 24 causes the blades 18 to pass in front of the pixel array 32, and the processor 54 can include an image trigger 60 having a trigger signal generator to simultaneously trigger the pixels 34 in the pixel array 32 to simultaneously obtain a plurality of the intensity-based signals from the pixels 34, which are converted and stored as a single scan line image at predetermined times. Further, rotor position information can be provided to the processor 54 from a sensor 62 on the rotor 24, such as from a shaft position signal generator, in order to synchronize reception of the intensity-based line images to the rotational speed of the rotor 24. Hence, a succession of intensity-based line images can be stored in the image storage 58 as a blade 18 is rotated past the pixel array 32 wherein the intensity-based line images with each line image forming a full length fast scan width image of the blade airfoil 48 in the radial direction, and the rotation of the blade 18 represents a slow scan direction with each line in the slow scan direction having a width of one pixel. For rotor rotation at speeds of about 2-3 rpm, the image trigger 60 may operate to obtain the intensity based line images at a rate of about 300,000 line images per second.

The processor 54 can further include an image analyzer 64 configured to convert the succession of intensity-based line images into a cohesive two-dimensional digital image of the blade airfoil 48, which can be used in an inspection analysis of the blade 18. In particular, the intensity-based line images can be stitched together, combining the plurality of line images of successive image areas 46 obtained in the slow scan direction, to form a blade image that may be used to identify a defect in the surface, such as a crack, damage to a coating, etc., as is depicted by an exemplary defect 66 on the surface of the airfoil 48 in FIG. 3. Further, since the pixels 34 can be located in close proximity to the blade 18 and individually respond with a high sensitivity to variations in light intensity, a corresponding improved contrast two-dimensional image can be provided.

Figure 4:
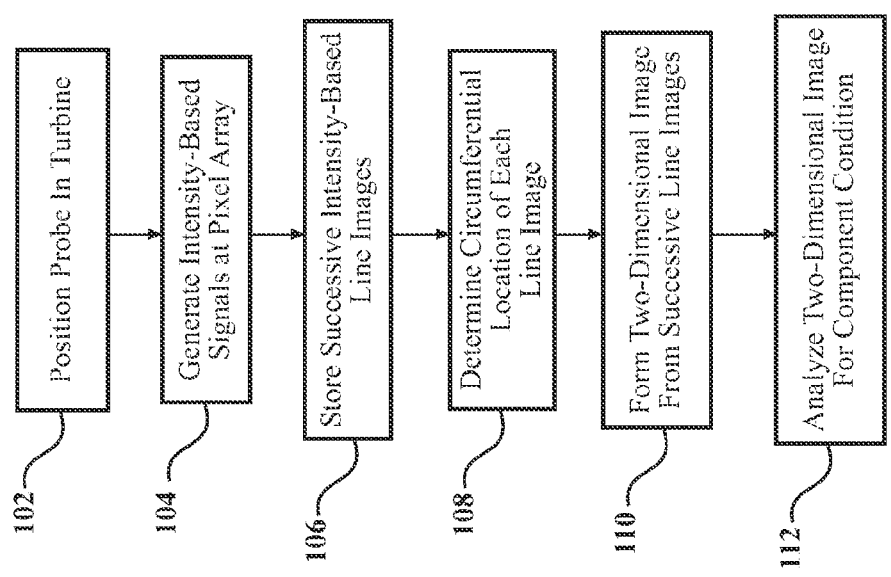
FIG. 4 is a flowchart of an exemplary process for inspecting a component in accordance with aspects of the present invention.

FIG. 4 is a flowchart of an exemplary process for forming a two-dimensional image for inspection of a component of a turbine in accordance with the principles of the present invention. In step 102, a probe comprising a one-dimensional pixel array is positioned within a turbine such that a turbine component supported on the rotor can be scanned. In particular, the one-dimensional pixel array is positioned so that it receives reflected energy from an image area of a component of the turbine. In step 104, a turning gear operation is performed and successive groups of intensity-based signals are generated by the pixel array. In step 106, the intensity-based signals are converted to image-based line images that are stored. The intensity-based line images correspond to an image area, where the line images can be captured at a controlled time so that each line image corresponds to a known shaft rotational position and to a corresponding location on the component. Thus, in step 108, the circumferential position of a captured line image can be determined. In this way, a scanned image of the entire component surface can be constructed in a two-dimensional image, in step 110, by combining the one-dimensional (single-pixel array) images together such that they are ordered in their circumferential position. In step 112, the two-dimensional image can be used to analyze the component to identify the condition of the component, including identification of deterioration or defects in the component.

Figure 5:
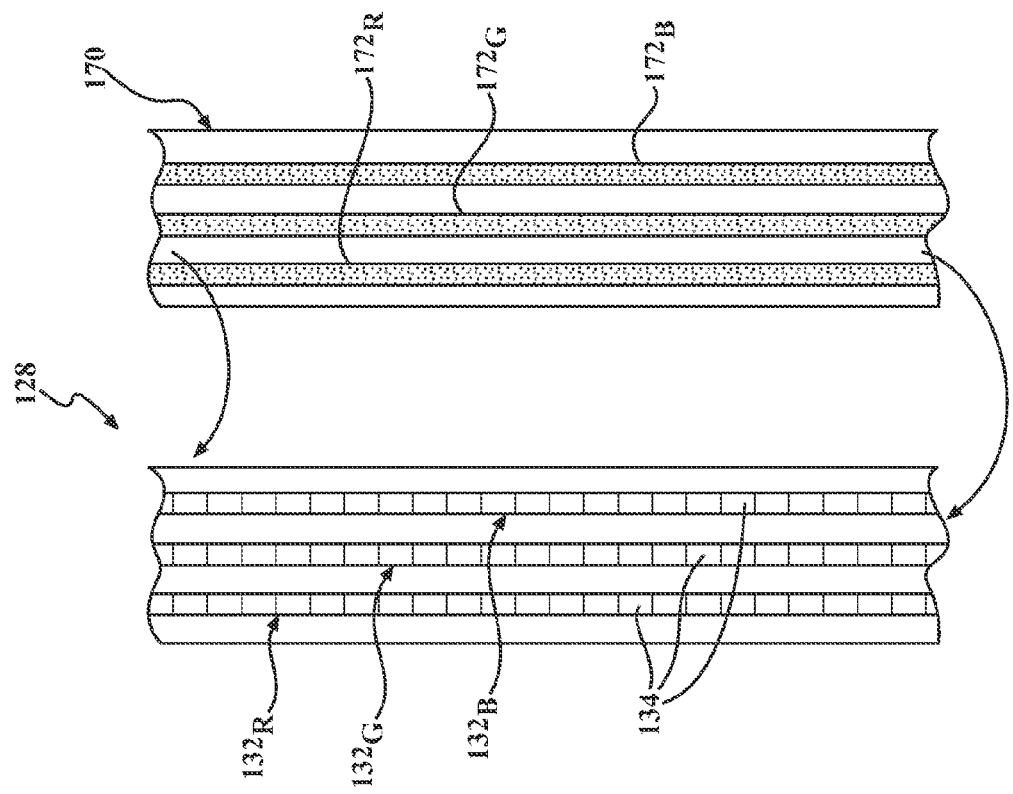
FIG. 5 is a partially exploded view of a portion of a modified probe in accordance with aspects of the present invention.

Referring to FIG. 5, a modification of the above-described probe 28 may be formed to provide a two-dimensional color image of the component being inspected. FIG. 5 illustrates a portion of a modified probe 128 having three separate one-dimensional (single-pixel) arrays $132_R$, $132_G$, $132_B$ for receiving filtered light from an image area 46 at frequencies corresponding to red, green and blue light. The pixel arrays $132_R$, $132_G$, $132_B$ can be substantially identical, each being formed of a plurality of pixels 134 extending single file along the length of the probe 128 in a manner similar to that described above for the pixels 34 of the pixel array 32 on the probe 28. A filter structure 170 including elongated red, green and blue filter elements $172_R$, $172_G$, $172_B$, respectively, can be provided positioned over the respective pixel arrays $132_R$, $132_G$, $132_B$, i.e., between the probe 128 and the component. The filter structure 170 can selectively filter light passing through the filter elements $172_R$, $172_G$, $172_B$ into red, green and blue components of the light spectrum for transmission onto the respective pixel arrays $132_R$, $132_G$, $132_B$. Additionally, a lens or lenses (not shown) can be provided for focusing the reflected light from the image area 46 to the pixel arrays $132_R$, $132_G$, $132_B$.

The pixels 134 of the pixel arrays $132_R$, $132_G$, $132_B$ provide intensity-based signals to the processor 54 where the intensity-based signals are converted to image-based line images that are stored. It may be understood that, for each image area 46, an image-based line image can be formed and stored for the pixel arrays $132_R$, $132_G$, $132_B$. Hence, a red, green and blue line image is associated with the location of each image area 46, and can be converted and stored as a data file in the form of a digitized line image comprising a single scan line image where, for each pixel in the stored line image, the data file can include information on the intensity value for each pixel and its color or grayscale shade. The succession of intensity-based line images received from the arrays $132_R$, $132_G$, $132_B$ are converted into a cohesive two-dimensional color image of the component in a manner similar to that described above for the probe 28.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of inspecting a component located on a rotor rotating about an axis internal to a turbine, comprising:
    providing an elongated probe defining a probe length and having a one-dimensional pixel array formed by a plurality of pixels extending single file along the probe length;
    positioning the probe through an access port in a casing of the turbine;
    rotating the rotor to move the component past the pixel array;
    receiving at the pixel array energy emitted from an image area defined by a line extending along the component and lying in a plane extending parallel to radial and axial directions in the turbine;
    conveying an intensity-based signal from each pixel in the pixel array to a processor to convert the intensity-based signals to an intensity-based line image; and
    converting a succession of the intensity-based line images into a cohesive two-dimensional digital image of the component.

2. The method of claim 1, wherein the component is a turbine blade and the probe is positioned with the probe length extending radially from the casing toward the rotor.

3. The method of claim 2, wherein the turbine blade includes a blade length extending from a radially inner platform to a radially outer blade tip, and the pixel array extends the length of the blade from the platform to the blade tip.

4. The method of claim 3, wherein the pixel array has a length of about 12 inches.

5. The method of claim 1, wherein rotation of the rotor is performed during a turning gear operation of the turbine.

6. The method of claim 1, including a lens positioned between the component and the pixel array, and the lens focusing light energy received from the image area into a line on the pixel array.

7. The method of claim 1, wherein conveying the intensity-based signal from the pixel array and conversion to the intensity-based line images is synchronized to a rotation speed of the rotor.

8. The method of claim 1, including elongated red, green and blue filters extending along the probe length, and a one-dimension pixel array associated with each filter and receiving energy passing through an associated filter from the component, and including converting a succession of intensity-based line images received from the arrays into a cohesive color image of the component.

9. A system for inspecting a component located on a rotor rotating about an axis internal to a turbine, comprising:
    an elongated probe having a one-dimensional pixel array formed by a plurality of pixels extending single file along a length dimension of the probe;
    wherein the probe is positioned between a casing and a rotor of the turbine and extends in a plane that is parallel to radial and axial directions in the turbine;
    the pixel array configured to receive energy emitted from an image area defined by a line extending along the component and lying in the plane of the probe;
    an array conduit configured to convey an intensity-based signal from each pixel in the pixel array to a distal end of the array conduit; and
    a processor connected to the distal end of the array conduit outside of the turbine and configured to convert a succession of the intensity-based signals into a succession of corresponding intensity-based line images for formation of a cohesive two-dimension digital image of the component.

10. The system of claim 9, wherein the component is a turbine blade and the probe is positioned with the length dimension extending radially from the casing toward the rotor.

11. The system of claim 10, wherein the turbine blade includes a blade length extending from a radially inner platform to a radially outer blade tip, and the pixel array extends the length of the blade from the platform to the blade tip.

12. The method of claim 11, wherein the pixel array has a length of about 12 inches.

13. The system of claim 9, wherein the turbine includes a turning gear operating to rotate the component relative to the probe.

14. The system of claim 9, including a lens positioned between the component and the pixel array, and the lens configured to focus light energy received from the image area into a line on the pixel array.

15. The system of claim 9, wherein the processor is configured to synchronize to a rotation speed of the rotor conversion of the intensity-based signals from the pixel array into intensity-based line images.

16. The system of claim 9, including elongated red, green and blue filters extending along the probe length, and a one-dimension pixel array associated with each filter and receiving energy passing through an associated filter from the component, wherein the processor is configured to convert a succession of intensity-based line images received from the arrays into a cohesive color image of the component.

17. The system of claim 9, further comprising:
    a shaft position signal generator configured to generate a position signal indicating a predetermined rotational position of the rotor;
    a trigger signal generator associated with the processor configured to transmit trigger signals to the pixels in the pixel array to generate the intensity-based signals of the pixel array, wherein the trigger signal generator transmits a plurality of trigger signals to cause the processor to capture a plurality of intensity-based signals from the pixel array;
    the trigger signal generator further configured to transmit each of the plurality of trigger signals at a respective time based on the position signal so that each respective trigger signal corresponds to a respective rotational position of the shaft; and
    the processor including an image analyzer configured to create a two-dimensional image of the rotating component by arranging the plurality of intensity-based line images obtained from the intensity-based signals in order according to the respective corresponding rotational position for each of the plurality of intensity-based line images.

18. A method of inspecting a turbine blade located on a rotor rotating about an axis internal to a turbine, the turbine blade including a radially elongated airfoil supported to a blade platform and defining a blade tip opposite the platform, the method comprising:
  providing an elongated probe defining a probe length and having a one-dimensional pixel array formed by a plurality of pixels extending single file along the probe length, wherein a length of the pixel array is generally the same as a length of the airfoil between the blade platform and the blade tip;
  positioning the probe through an access port in a casing of the turbine;
  rotating the rotor to move the turbine blade past the pixel array;
  receiving at the pixel array energy emitted from an image area defined by a radially extending line extending along the airfoil;
  conveying an intensity-based signal from each pixel in the pixel array to a processor to convert the intensity-based signals to an intensity-based line image; and
  converting a succession of the intensity-based line images into a cohesive two-dimensional digital image of the airfoil.

19. The method of claim 18, wherein conveying the intensity-based signal from the pixel array and conversion to the intensity-based line images is synchronized to a rotation speed of the rotor.

* * * * *